United States Patent
Kanda

(10) Patent No.: US 11,033,469 B2
(45) Date of Patent: Jun. 15, 2021

(54) COSMETIC FOR HAIR DYEING OR HAIR BLEACHING

(71) Applicant: KAO CORPORATION, Chuo-ku (JP)

(72) Inventor: Takashi Kanda, Ichikawa (JP)

(73) Assignee: KAO CORPORATION, Chuo-ku (JP)

(*) Notice: Subject to any disclaimer, the term of this patent is extended or adjusted under 35 U.S.C. 154(b) by 341 days.

(21) Appl. No.: 16/084,794

(22) PCT Filed: Mar. 14, 2017

(86) PCT No.: PCT/JP2017/010160
§ 371 (c)(1),
(2) Date: Sep. 13, 2018

(87) PCT Pub. No.: WO2017/159670
PCT Pub. Date: Sep. 21, 2017

(65) Prior Publication Data
US 2019/0125635 A1    May 2, 2019

Related U.S. Application Data

(60) Provisional application No. 62/308,511, filed on Mar. 15, 2016, provisional application No. 62/447,090, filed on Jan. 17, 2017.

(51) Int. Cl.
| | | |
|---|---|---|
| A61K 8/22 | (2006.01) | |
| A61Q 5/08 | (2006.01) | |
| A61K 8/86 | (2006.01) | |
| A61K 8/44 | (2006.01) | |
| A61K 8/81 | (2006.01) | |
| A61K 8/39 | (2006.01) | |
| A61Q 5/10 | (2006.01) | |
| A61K 8/34 | (2006.01) | |
| A61K 8/41 | (2006.01) | |
| A61K 8/46 | (2006.01) | |
| A61Q 5/06 | (2006.01) | |

(52) U.S. Cl.
CPC ............ *A61K 8/22* (2013.01); *A61K 8/342* (2013.01); *A61K 8/39* (2013.01); *A61K 8/415* (2013.01); *A61K 8/416* (2013.01); *A61K 8/44* (2013.01); *A61K 8/442* (2013.01); *A61K 8/463* (2013.01); *A61K 8/81* (2013.01); *A61K 8/817* (2013.01); *A61K 8/86* (2013.01); *A61Q 5/065* (2013.01); *A61Q 5/08* (2013.01); *A61Q 5/10* (2013.01); *A61K 2800/432* (2013.01); *A61K 2800/882* (2013.01)

(58) Field of Classification Search
CPC . A61K 8/22; A61K 8/342; A61K 8/39; A61K 8/415; A61K 8/416; A61K 8/44; A61K 8/442; A61K 8/463; A61K 8/81; A61K 8/817; A61K 8/86; A61Q 5/065; A61Q 5/08; A61Q 5/10
See application file for complete search history.

(56) References Cited

U.S. PATENT DOCUMENTS

| | | |
|---|---|---|
| 2011/0168201 A1 | 7/2011 | Bureiko et al. |
| 2012/0207689 A1* | 8/2012 | Konno .............. A61K 8/22 424/62 |
| 2013/0125918 A1 | 5/2013 | Nobuto et al. |
| 2016/0166484 A1 | 6/2016 | Izumi et al. |
| 2016/0262994 A1 | 9/2016 | Ogawa et al. |
| 2016/0271048 A1 | 9/2016 | Ogawa et al. |

FOREIGN PATENT DOCUMENTS

| | | |
|---|---|---|
| JP | 2002-114644 A | 4/2002 |
| JP | 2002-241248 A | 8/2002 |
| JP | 2012-72128 A | 4/2012 |
| JP | 2012-97024 A | 5/2012 |
| JP | 2013-516434 A | 5/2013 |
| JP | 2013-184967 A | 9/2013 |
| JP | 2015-44806 A | 3/2015 |
| JP | 2015-107961 A | 6/2015 |
| JP | 2015-107962 A | 6/2015 |

OTHER PUBLICATIONS

International Search Report dated May 16, 2017 in PCT/JP2017/010160 filed Mar. 14, 2017.

* cited by examiner

*Primary Examiner* — Genevieve S Alley
(74) *Attorney, Agent, or Firm* — Oblon, McClelland, Maier & Neustadt, L.L.P.

(57) ABSTRACT

A cosmetic product for hair dyeing or hair bleaching comprising a first agent containing an alkali agent and a second agent containing hydrogen peroxide, wherein viscosity of any one of the first agent and the second agent is 100 mPa·s or less, and viscosity of the other agent is 1000 mPa·s or more, the cosmetic product comprising components (A) to (D) in a mixture of the first agent and the second agent, wherein the mass ratio of [(B)+(C)]/(A) in the mixture is 2 or more and 11 or less:

(A) a polymer containing a diallyl quaternary ammonium salt as a constitutional unit and having a charge density of 2.5 meq/g or more and 9 meq/g or less, (B) a compound represented by formula (3):

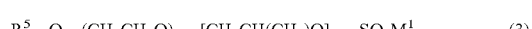

$$R^5-O-(CH_2CH_2O)_n-[CH_2CH(CH_3)O]_m-SO_3M^1 \quad (3)$$

wherein $R^5$ represents a $C_{8-25}$ hydrocarbon group, n represents an average addition molar number of 0 to 50, m represents an average addition molar number of 0 to 50, and $M^1$ represents an alkali metal or $NH_4$, (C) an anionic surfactant having carboxy group(s), and (D) a polyoxyethylene-based nonionic surfactant wherein the average addition molar number of the oxyethylene group is 90 or more and 250 or less.

21 Claims, No Drawings

COSMETIC FOR HAIR DYEING OR HAIR BLEACHING

TECHNICAL FIELD

The present invention relates to a cosmetic product for hair dyeing or hair bleaching.

BACKGROUND ART

Oxidative hair dyes and hair bleaches in which two or more agents are mixed together immediately prior to use have been widely used for hair dyeing and bleaching. In such oxidative hair dyes and hair bleaches, a first agent containing an alkali and a second agent containing hydrogen peroxide are mixed together to activate hydrogen peroxide, and then hair melanin is decomposed and an oxidative dye is polymerized on hair of the head, which results in very efficient change in hair color.

However, it is widely known that when oxidative hair dyes and hair bleaches are used, hair fibers are damaged by activated hydrogen peroxide. There is a problem that when hair damaged by oxidation receives another hair dyeing treatment or bleaching treatment after a certain period, excessive dye penetration or excessive bleaching can occur, leading to fail in achieving an expected color.

With respect to such problems, a method has been proposed which includes applying oxidative hair dyes or hair bleaches only to a newly grown portion of hair having no oxidative damage and allowing the hair dyes or hair bleaches to stand for a certain period, and then applying the oxidative hair dyes or hair bleaches again to a previously dyed portion of hair. However, the method requires two separate applications of oxidative hair dyes or hair bleaches, leading to complicated procedure and labor. Further, there are proposed methods including a method of preliminary treating a portion of hair which has received one or more hair dyeing treatments or bleaching treatments with keratin hydrolysate (Patent Literature 1), and a method of applying an alkaline oxidative hair dye composition to a newly grown hair and applying a slightly alkaline oxidative hair dye composition to a previously dyed hair (Patent Literature 2). These methods also require two separate applications of agents to hair, and thus the complication cannot be avoided.

CITATION LIST

Patent Literature

Patent Literature 1: JP 2002-114644 A
Patent Literature 2: JP 2002-241248 A

SUMMARY OF THE INVENTION

The present invention provides a cosmetic product for hair dyeing or hair bleaching, which comprises
a first agent comprising an alkali agent and a second agent comprising hydrogen peroxide,
wherein viscosity at 25° C. of one of the first agent and the second agent is 100 mPa·s or less and viscosity at 25° C. of the other agent is 1000 mPa·s or more,
the cosmetic product comprises the following components (A) to (D) in a mixture of the first agent and the second agent, and a mass ratio of a total amount of the component (B) and the component (C) to the component (A), [(B)+(C)]/(A), in the mixture is 2 or more and 11 or less:

(A) a polymer comprising a diallyl quaternary ammonium salt as a constitutional unit and having a charge density of 2.5 meq/g or more and 9 meq/g or less,
(B) a compound represented by the following general formula (3):

$$R^5-O-(CH_2CH_2O)_n-[CH_2CH(CH_3)O]_m-SO_3M^1 \qquad (3)$$

wherein $R^5$ represents a hydrocarbon group having 8 or more and 25 or less carbon atoms, n represents an average addition molar number of 0 or more and 50 or less, m represents an average addition molar number of 0 or more and 50 or less, and M represents an alkali metal or $NH_4$,
(C) an anionic surfactant having carboxy group(s), and
(D) a polyoxyalkylene-based nonionic surfactant wherein the average addition molar number of the oxyethylene group is 90 or more and 250 or less.

Further, the present invention provides a method of using the above-described cosmetic product for hair dyeing or hair bleaching, the method including applying the total amount of the mixture of the first agent and the second agent to a root of hair.

Further, the present invention provides a method of hair dyeing or hair bleaching including the following steps (a) and (b):
(a) a step of mixing the first agent and the second agent of the above-described cosmetic product for hair dyeing or hair bleaching in a main body of a container, and
(b) a step of extruding the above-described mixture from an applicator including the above-described main body of the container equipped with a cap unit having a tapered nozzle to apply the mixture to the root of hair.

DESCRIPTION OF THE INVENTION

The present inventors thought that if an oxidative hair dyes or hair bleaches can be applied only to a newly grown portion of hair having no oxidative damage (the root of hair) and allowing the mixture to stand for a certain period, and then the applied agents can be spread over a previously dyed portion of hair (hair tip), a high dyeing or bleaching effect can be exerted on the newly grown portion of hair, whereas a mild dyeing or bleaching effect can be provided to the previously dyed portion of hair, and thus uniform dyeing of the newly grown portion of hair and the previously dyed portion of hair is made possible without performing two separate applications.

However, if the oxidative hair dyes or hair bleaches have reduced viscosity for the purpose of improving spreadability on hair of the head, dripping can occur. On the other hand, if the oxidative hair dyes or hair bleaches have high viscosity for the purpose of suppressing dripping, uniform spreading up to hair tip can be difficult.

The present invention relates to a cosmetic product for hair dyeing or hair bleaching which can be excellently spread over a whole hair uniformly, in which the cosmetic product can be easily applied to the root of hair exactly without dripping, whereas it can be easily spread up to the hair tip even after the product has been left around the root for a certain period.

The present inventors have found that a cosmetic product for hair dyeing or hair bleaching which satisfies the aforementioned requirements can be obtained by using a specific cationic polymer, specific two types of anionic surfactants, and a specific nonionic surfactant in combination, and controlling the ratio between the above-described cationic polymer and the above-described two types of anionic surfactants within a certain range. That is, a cosmetic product for hair dyeing or hair bleaching of the present invention can be easily applied to the root of hair and the hairline exactly without dripping at initial stage of application to hair of the head. In addition, even if the agent has been left for a certain period after application for sufficient dyeing of the root of hair and the hairline, which are resistant to dyeing, the agent is in a state that the agent can be easily spread by sharing out toward hair tip using fingers or a comb. Consequently, even an inexperienced user can achieve uniform dyeing or bleaching of whole hair of the head.

A cosmetic product for hair dyeing or hair bleaching of the present invention can be used as a two-agent cosmetic product in which a first agent and a second agent are mixed together before use, or as a three-agent cosmetic product in which a third agent such as a granulated substance of, for example, a persulfate is further mixed together before use in addition to the first agent and the second agent. In the present invention, a mixture of a first agent and a second agent refers to a mixture of a first agent and a second agent in a two-agent cosmetic product, and it refers to a mixture of a first agent, a second agent, and a third agent in a three-agent cosmetic product.

[Alkali Agent]

The first agent contains an alkali agent. Examples of the alkali agent include ammonia and salts thereof (e.g., ammonium hydrogencarbonate); alkanolamines such as monoethanolamine, isopropanolamine, 2-amino-2-methyl propanol, and 2-aminobutanol, and salts thereof; alkanediamines such as 1,3-propanediamine, and salts thereof; and carbonates such as guanidine carbonate, sodium carbonate, potassium carbonate, sodium hydrogencarbonate, and potassium hydrogencarbonate. These alkali agents may be used alone or in combination of two or more. From the viewpoint of a sufficient hair dyeing effect, the content of the alkali agent in the mixture of the first agent and the second agent is preferably 0.05% by mass or more, more preferably 0.10% by mass or more, and even more preferably 0.20% by mass or more, and in terms of reduction in hair damage or scalp irritation, it is preferably 15% by mass or less, more preferably 10% by mass or less, and even more preferably 5% by mass or less.

[Hydrogen Peroxide]

The second agent contains hydrogen peroxide. From the viewpoint of a sufficient hair bleaching effect, the content of hydrogen peroxide in the second agent is preferably 1% by mass or more, and more preferably 3% by mass or more, and it is preferably 12% by mass or less, and more preferably 9% by mass or less. The content of hydrogen peroxide in the mixture of the first agent and the second agent is preferably 1% by mass or more, and more preferably 2% by mass or more, and it is preferably 8% by mass or less, and more preferably 6% by mass or less.

[Component (A): Polymer Containing Diallyl Quaternary Ammonium Salt as a Constitutional Unit]

The cosmetic product for hair dyeing or hair bleaching of the present invention contains a polymer containing a diallyl quaternary ammonium salt as a constitutional unit in the mixture of the first agent and the second agent and having a charge density of 2.5 meq/g or more and 9 meq/g or less. The charge density used herein in the present invention refers to the number of moles of cationic groups per gram of polymer×1000 (meq/g). The polymer containing a diallyl quaternary ammonium salt as a constitutional unit in the present invention also includes a polymer further containing a constitutional unit having a cationic group other than diallyl quaternary ammonium salts, and a constitutional unit having an anionic group and/or a nonionic group. In the present invention, only the charge density of the cationic group is to be taken into consideration for these polymers, too.

From the viewpoint of both spreadability toward hair tip and resistance to dripping of the mixture applied to the root of hair, the charge density of the component (A) is 2.5 meq/g or more and 9 meq/g or less. It is preferably 3.0 meq/g or more, more preferably 3.5 meq/g or more, and even more preferably 4.5 meq/g or more. It is preferably 8.0 meq/g or less, more preferably 7.0 meq/g or less, even more preferably 6.5 meq/g or less, even more preferably 6.0 meq/g or less, and even more preferably 5.5 meq/g or less.

The polymer of the component (A) is a polymer having a backbone represented by the following general formula (1) or (2):

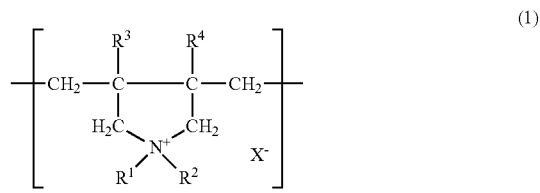

(1)

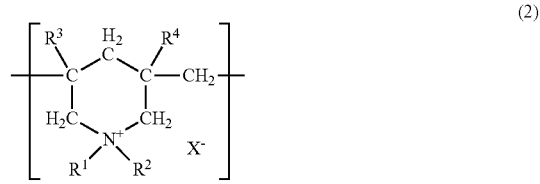

(2)

wherein $R^1$ and $R^2$ may be the same or different and represent a hydrogen atom, or an alkyl group, an aryl group (e.g., a phenyl group), a hydroxyalkyl group, an amidoalkyl group, a cyanoalkyl group, an alkoxyalkyl group, or a carboalkoxyalkyl group having 1 or more and 18 or less carbon atoms, $R^3$ and $R^4$ may be the same or different and represent a hydrogen atom, an alkyl group having 1 or more and 3 or less carbon atoms, or a phenyl group, and $X^-$ represents an anion (e.g., chloride ion, bromide ion, iodide ion, sulfate anion, sulfonate anion, methylsulfate anion, phosphoric acid anion, and nitrate anion).

From the viewpoint of spreadability toward hair tip and resistance to dripping of the mixture applied to the root of hair, the polymer of the component (A) contains a constitutional unit represented by the formula (1) or (2) in an amount of preferably from 20 to 100 mol %, more preferably from 30 to 100 mol %, and even more preferably from 50 to 100 mol % in one molecule.

The polymer of the component (A) is preferably a homopolymer of a diallyl quaternary ammonium salt, a copolymer of a diallyl quaternary ammonium salt and acrylic acid, and a copolymer of a diallyl quaternary ammonium salt and acrylamide.

The copolymer of a diallyl quaternary ammonium salt and acrylic acid is preferably, for example, a copolymer represented by the following general formula (1a) or (2a). The copolymer of a diallyl quaternary ammonium salt and acrylamide is preferably, for example, a copolymer represented by the following general formula (1b) or (2b):

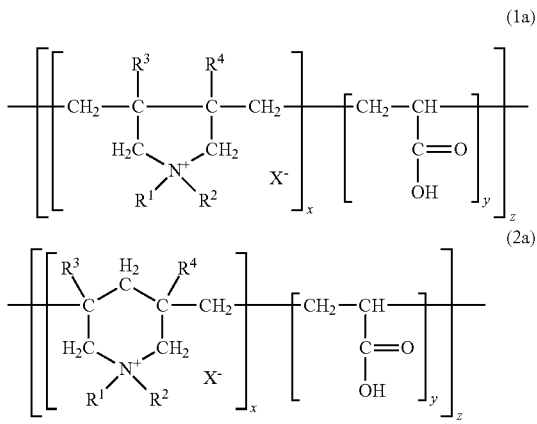

(1a)

(2a)

wherein $R^1$, $R^2$, $R^3$, $R^4$, and $X^-$ have the same meaning as described above. x and y each represents a number of from 1 to 99, and z represents a number of from 150 to 8,000.

From the viewpoint of spreadability toward hair tip and resistance to dripping of the mixture applied to the root of hair, the ratio between x and y (x:y) is preferably from 50:50 to 95:5, more preferably from 55:45 to 90:10, and even more preferably from 60:40 to 85:15.

The x and y may be incorporated in block form or random form.

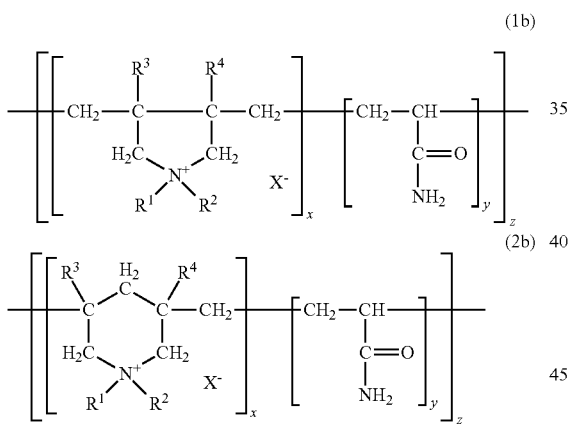

(1b)

(2b)

wherein $R^1$, $R^2$, $R^3$, $R^4$, and $X^-$ have the same meaning as described above. x and y each represents a number of 1 to 99, and z represents a number of 150 to 8,000.

From the viewpoint of spreadability toward hair tip and resistance to dripping of the mixture applied to the root of hair, the ratio between x and y (x:y) is preferably from 10:90 to 90:10, more preferably from 15:85 to 80:20, and even more preferably from 20:80 to 70:30.

The x and y may be incorporated in block form or random form.

From the viewpoint of spreadability toward hair tip and resistance to dripping of the mixture applied to the root of hair, the weight-average molecular weight of the component (A) is preferably 40,000 or more, more preferably 200,000 or more, even more preferably 400,000 or more, even more preferably 2,000,000 or more, and even more preferably 4,000,000 or more. It is preferably 50,000,000 or less, more preferably 10,000,000 or less, and even more preferably 5,000,000 or less.

Here, the weight-average molecular weight can be measured by, for example, gel permeation chromatography (GPC) under the following conditions.

Mobile phase: 50 mM of LiBr, 1% by mass of $CH_3COOH$/ethanol:water=3:7

Column: TSK gel α-M (two columns in series)

Reference material: polyethylene glycol

Specific examples of the component (A) include Merquat 100 (manufactured by The Lubrizol Corporation, a homopolymer of diallyl quaternary ammonium), Merquat 280 and Merquat 295 (manufactured by The Lubrizol Corporation, copolymers of a diallyl quaternary ammonium salt and acrylic acid), and Merquat 740 and Merquat 550 (manufactured by The Lubrizol Corporation, copolymers of a diallyl quaternary ammonium salt and acrylamide).

The component (A) may be used alone or in combination of two or more. The component (A) may be included in any of the first agent, the second agent, and the third agent of the cosmetic product for hair dyeing or hair bleaching of the present invention. From the viewpoint of spreadability toward hair tip and resistance to dripping of the mixture applied to the root of hair, it is preferably included in the first agent.

From the viewpoint of spreadability toward hair tip and resistance to dripping of the mixture applied to the root of hair, the content of the component (A) in the mixture of the first agent and the second agent is preferably 0.10% by mass or more, more preferably 0.125% by mass or more, and even more preferably 0.15% by mass or more, and it is preferably 5% by mass or less, more preferably 4% by mass or less, even more preferably 3% by mass or less, even more preferably 2% by mass or less, and even more preferably 1% by mass or less.

[Component (B): Compound Represented by General Formula (3)]

The cosmetic product for hair dyeing or hair bleaching of the present invention contains a compound represented by the following general formula (3) in the mixture of the first agent and the second agent:

$$R^5-O-(CH_2CH_2O)_n-[CH_2CH(CH_3)O]_m-SO_3M^1 \quad (3)$$

wherein $R^5$ represents a hydrocarbon group having 8 or more and 25 or less carbon atoms, n represents an average addition molar number of 0 or more and 50 or less, m represents an average addition molar number of 0 or more and 50 or less, and M represents an alkali metal or $NH_4$.

From the viewpoint of spreadability toward hair tip and resistance to dripping of the mixture applied to the root of hair, the number of carbon atoms of $R^5$ in the general formula (3) is 8 or more, and preferably 10 or more, and it is 25 or less, preferably 24 or less, more preferably 22 or less, and even more preferably 18 or less. $R^5$ is preferably a linear or branched alkyl or alkenyl group, and more preferably a linear alkyl group.

From the viewpoint of spreadability toward hair tip and resistance to dripping of the mixture applied to the root of hair, n in the general formula (3) is preferably 0.5 or more, and more preferably 1 or more, and it is preferably 45 or less, more preferably 30 or less, even more preferably 15 or less, even more preferably 10 or less, even more preferably 8 or less, and even more preferably 6 or less.

From the viewpoint of spreadability toward hair tip and resistance to dripping of the mixture applied to the root of hair, m in the general formula (3) is preferably 30 or less, more preferably 10 or less, even more preferably 5 or less, and even more preferably 0.

$M^1$ in the general formula (3) is a salt-forming cation group, and is an alkali metal or $NH_4$. Examples of the alkali metal include sodium, potassium, and lithium. From the viewpoint of spreadability toward hair tip and resistance to dripping of the mixture applied to the root of hair, inter alia, it is more preferably sodium and potassium, and even more preferably sodium.

The $(CH_2CH_2O)$ and $[CH_2CH(CH_3)O]$ in the component (B) may be incorporated in block form or random form.

The component (B) may be used alone or in combination of two or more. The component (B) may be included in any of the first agent, the second agent, and the third agent of the cosmetic product for hair dyeing or hair bleaching of the present invention. From the viewpoint of spreadability toward hair tip and resistance to dripping of the mixture applied to the root of hair, it is preferably included in the first agent.

From the viewpoint of spreadability toward hair tip and resistance to dripping of the mixture applied to the root of hair, the content of the component (B) in the mixture of the first agent and the second agent is preferably 0.05% by mass or more, more preferably 0.1% by mass or more, even more preferably 0.2% by mass or more, even more preferably 0.3% by mass or more, even more preferably 0.5% by mass or more, even more preferably 0.8% by mass or more, and even more preferably 1.0% by mass or more, and it is preferably 10% by mass or less, more preferably 8% by mass or less, even more preferably 6% by mass or less, even more preferably 5% by mass or less, even more preferably 4% by mass or less, and even more preferably 3% by mass or less.

[Component (C): Anionic Surfactant Having Carboxy Group(s)]

The cosmetic product for hair dyeing or hair bleaching of the present invention contains an anionic surfactant having carboxy group(s) in the mixture of the first agent and the second agent. Inter alia, at least one compound selected from the group consisting of an N-acylamino acid salt, an N-acyl-N-alkylamino acid salt, and an alkylether carboxylic acid salt is preferably included.

Examples of the amino acid residue of the N-acylamino acid salt include residues such as glutamic acid and aspartic acid. Examples of the amino acid residue of the N-acyl-N-alkylamino acid salt include residues such as glutamic acid, glycine, and (β-alanine. The alkyl group of the N-acyl-N-alkylamino acid salt is preferably an alkyl group having 1 to 3 carbon atoms and includes methyl, ethyl, propyl, and isopropyl groups. The acyl group is preferably an acyl group having 12 to 18 carbon atoms and includes, for example, a lauroyl, myristoyl, and palmitoyl group, and examples of the salts thereof include salts of sodium, potassium, lithium, ethanolamine, diethanolamine, and triethanolamine. Specific examples include N-acylamino acid including N-lauroyl glutamic acid, N-myristoyl glutamic acid, and N-cocoyl glutamic acid, and N-acyl-N-alkylamino acid including N-lauroyl-N-isopropyl glycine, N-lauroylsarcosine, N-myristoylsarcosine, N-palmitoylsarcosine, N-lauroyl-N-methyl-β-alanine.

The alkylether carboxylic acid salt includes a compound represented by the following general formula (4):

$$R^6-Z-(CH_2CH_2O)_q-CH_2COOM^2 \qquad (4)$$

wherein $R^6$ represents a linear or branched alkyl group or alkenyl group having 7 or more and 19 or less carbon atoms, Z represents $-O-$ or $-CONH-$, $M^2$ represents a hydrogen atom, an alkali metal, triethanolamine, or ammonium, and q represents a number of 1 or more and 20 or less.

In the above-described general formula (4), the number of carbon atoms of $R^6$ is 7 or more, and preferably 11 or more, and 19 or less, and preferably 15 or less. q is 1 or more, preferably 3 or more, and more preferably 6 or more, and 20 or less, preferably 15 or less, and more preferably 12 or less. Specific examples of the compound represented by the general formula (4) include polyoxyethylene(10) lauryl ether carboxylic acid (in the general formula (4), $R^6=C_{12}H_{25}$, $Z=-O-$, and q=10), polyoxyethylene(8) myristyl ether carboxylic acid (in the general formula (4), $R^6=C_{14}H_{29}$, $Z=-O-$, and q=8), laurylamidopolyoxyethylene(6) ether carboxylate (in the general formula (4), $R^6=C_{11}H_{23}$, $Z=-CONH-$, and q=6), laurylamidopolyoxyethylene(10) ether carboxylate (in the general formula (4), $R^6=C_{11}H_{23}$, $Z=-CONH-$, and q=10). Neutralization degree thereof is preferably 60 to 120%, and $M^2$ is preferably an alkali metal, and more preferably potassium.

The component (C) may be used alone or in combination of two or more. The component (C) may be included in any of the first agent, the second agent, and the third agent of the cosmetic product for hair dyeing or hair bleaching of the present invention. From the viewpoint of spreadability toward hair tip and resistance to dripping of the mixture applied to the root of hair, it is preferably included in the first agent.

From the viewpoint of spreadability toward hair tip and resistance to dripping of the mixture applied to the root of hair, the content of the component (C) in the mixture of the first agent and the second agent is preferably 0.05% by mass or more, more preferably 0.10% by mass or more, even more preferably 0.2% by mass or more, even more preferably 0.3% by mass or more, even more preferably 0.5% by mass or more, even more preferably 0.6% by mass or more, and even more preferably 1.0% by mass or more, and it is preferably 10% by mass or less, more preferably 8% by mass or less, even more preferably 6% by mass or less, even more preferably 5% by mass or less, even more preferably 4% by mass or less, and even more preferably 3% by mass or less.

From the viewpoint of spreadability toward hair tip and resistance to dripping of the mixture applied to the root of hair, the content of the total amount of the components (B) and (C) in the mixture of the first agent and the second agent is preferably 0.1% by mass or more, more preferably 0.2% by mass or more, even more preferably 0.4% by mass or more, even more preferably 0.6% by mass or more, even more preferably 0.8% by mass or more, even more preferably 1.0% by mass or more, and even more preferably 2.0% by mass or more, and it is preferably 15% by mass or less, more preferably 10% by mass or less, even more preferably 8% by mass or less, even more preferably 6% by mass or less, and even more preferably 4% by mass or less.

From the viewpoint of resistance to dripping, the mass ratio of the component (B) to the total amount of the components (B) and (C), (B)/[(B)+(C)], in the mixture of the first agent and the second agent is preferably 0.1 or more, more preferably 0.2 or more, even more preferably 0.3 or more, and even more preferably 0.4 or more. From the viewpoint of changes of the agent in physical properties such as spreadability toward hair tip of the mixture applied to the root of hair, it is preferably 0.8 or less, more preferably 0.7 or less, and even more preferably 0.6 or less.

The mass ratio of the total amount of the components (B) and (C) to the component (A), [(B)+(C)]/(A), in the mixture of the first agent and the second agent, is 2 or more and 11 or less. From the viewpoint of changes of the agent in physical properties such as spreadability toward hair tip of the mixture applied to the root of hair, it is preferably 2.2 or more, more preferably 2.4 or more, even more preferably 2.6 or more, even more preferably 2.8 or more, even more preferably 3.0 or more, and even more preferably 4 or more. From the viewpoint of resistance to dripping, it is preferably 10 or less, and more preferably 9 or less. Due to the mass ratio within the above-described range, the mixture can be easily spread toward hair tip even if the mixture has been left for a certain period after application to the root of hair of the hairline.

[Component (D): Polyoxyethylene-Based Nonionic Surfactant]

The cosmetic product for hair dyeing or hair bleaching of the present invention contains a polyoxyethylene-based nonionic surfactant wherein the average addition molar number of the oxyethylene group is 90 or more and 250 or less in the mixture of the first agent and the second agent.

The polyoxyethylene-based nonionic surfactant wherein the average addition molar number of the oxyethylene group is 90 or more and 250 or less which can be used includes those represented by the following general formula (5):

$$R^7\text{—}O\text{—}(CH_2CH_2O)_r\text{—}H \quad (5)$$

wherein $R^7$ represents a linear or branched saturated or unsaturated hydrocarbon group having 8 or more and 22 or less carbon atoms, and r represents an average number of between 90 or more and 250 or less.

From the viewpoint of solubility of the dye contained in the hair dye, the number of carbon atoms in R' is preferably 10 or more, and more preferably 12 or more. It is preferably 20 or less, and more preferably 18 or less.

From the viewpoint of spreadability toward hair tip and resistance to dripping of the mixture applied to the root of hair, r is preferably 95 or more, and more preferably 100 or more. It is preferably 220 or less, more preferably 200 or less, and even more preferably 180 or less.

Specific examples of the polyoxyethylene-based nonionic surfactant include polyoxyethylene lauryl ether, polyoxyethylene cetyl ether, polyoxyethylene stearyl ether, and polyoxyethylene oleyl ether.

The polyoxyethylene-based nonionic surfactant of the component (D) may be used alone or in combination of two or more, and may be included in any of the first agent, the second agent, and the third agent. From the viewpoint of spreadability toward hair tip and resistance to dripping of the mixture applied to the root of hair, the content of the component (D) in the mixture of the first agent and the second agent is preferably 0.1% by mass or more, more preferably 0.2% by mass or more, even more preferably 0.3% by mass or more, and even more preferably 0.4% by mass or more. It is preferably 10% by mass or less, more preferably 8% by mass or less, even more preferably 6% by mass or less, even more preferably 4% by mass or less, and even more preferably 3% by mass or less.

[Component (E): Aliphatic Alcohol]

From the viewpoint of spreadability toward hair tip of the mixture applied to the root of hair, the cosmetic product for hair dyeing or hair bleaching of the present invention may contain an aliphatic alcohol having 12 or more and 24 or less carbon atoms as a component (E) in the mixture of the first agent and the second agent. The component (E) which can be used includes those represented by the following general formula (6):

$$R^8\text{—}OH \quad (6)$$

wherein $R^8$ represents a linear or branched hydrocarbon group having 12 or more and 24 or less carbon atoms.

From the viewpoint of spreadability toward hair tip of the mixture applied to the root of hair, the number of carbon atoms of $R^8$ in the general formula (6) is 12 or more, and preferably 14 or more. It is 24 or less, and preferably 22 or less. $R^8$ is preferably a linear or branched alkyl group or alkenyl group, and more preferably a linear alkyl group.

Specific examples of the aliphatic alcohol having 12 or more and 24 or less of carbon atoms include, for example, myristyl alcohol, cetanol, stearyl alcohol, arachidyl alcohol, behenyl alcohol, and oleyl alcohol.

The component (E) may be used alone or in combination of two or more, and may be included in any of the first agent, the second agent, and the third agent. From the viewpoint of spreadability toward hair tip of the mixture applied to the root of hair, it is preferably included in the second agent. From the viewpoint of spreadability toward hair tip of the mixture applied to the root of hair, the content of the component (E) in the mixture of the first agent and the second agent is preferably 0.5% by mass or more, more preferably 1.0% by mass or more, and even more preferably 1.5% by mass or more, and it is preferably 20% by mass or less, more preferably 15% by mass or less, even more preferably 10% by mass or less, and even more preferably 8% by mass or less.

[Component (F): Cationic Surfactant]

From the viewpoint of spreadability toward hair tip of the mixture applied to the root of hair, the cosmetic product for hair dyeing or hair bleaching of the present invention may contain a quaternary ammonium salt type cationic surfactant as a component (F) in the mixture of the first agent and the second agent. The cationic surfactant of the component (F) which can be used include those represented by the following general formula (7):

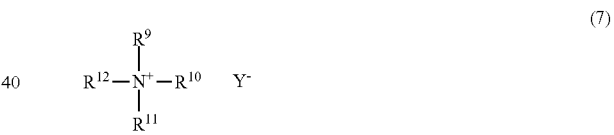

$$R^{12}\text{—}\overset{\overset{\displaystyle R^9}{|}}{\underset{\underset{\displaystyle R^{11}}{|}}{N^+}}\text{—}R^{10} \quad Y^- \quad (7)$$

wherein $R^9$, $R^{10}$, $R^{11}$, and $R^{12}$ each independently represent an optionally substituted hydrocarbon group, wherein one or two of the $R^9$, $R^{10}$, $R^{11}$, and $R^{12}$ have 8 or more and 36 or less carbon atoms, and the others have 1 or more and 7 or less carbon atoms. $Y^-$ represents an anion.

Examples of the hydrocarbon group include a linear or branched alkyl group, a linear or branched alkenyl group, an aryl group, and an aralkyl group. Examples of the substituent include a hydroxy group, an alkoxy group, an aryloxy group, an epoxy group, an amino group, a mono- or dialkylamino group, a trialkylammonium group, a fatty acid amido group, and a fatty acid ester group.

One or two (preferably one) of the $R^9$, $R^{10}$, $R^{11}$, and $R^{12}$ is a hydrocarbon group having 8 or more and 36 or less carbon atoms, preferably a linear or branched alkyl group. The number of carbon atoms is preferably 10 or more, and more preferably 12 or more. It is preferably 30 or less, more preferably 24 or less, and even more preferably 18 or less. The other groups are preferably alkyl groups having 1 or more and 3 or less carbon atoms, more preferably 1 or 2 carbon atoms, even more preferably 1 carbon atom.

Examples of the anion include chloride ion, bromide ion, iodide ion, methyl sulfate ion, ethyl sulfate ion, acetate ion, phosphate ion, sulfate ion, lactate ion, and saccharin ion.

Inter alia, from the viewpoint of availability, chloride son and bromide ion are preferable.

Specific examples of the component (F) include cetyltrimethylammonium chloride (INCI name: cetrimonium chloride), stearyltrimethylammonium chloride (INCI name: steartrimonium chloride), isostearyltrimethylammonium chloride (INCI name: isostearyltrimonium chloride), lauryltrimethylammonium chloride (INCI name: lauryltrimonium chloride), behenyltrimethylammonium chloride (INCI name: behentrimonium chloride), cocoyl trimethylammonium chloride (INCI name: cocotrimonium chloride), cetyltrimethylammonium bromide (INCI name: cetrimonium bromide), stearyltrimethylammonium bromide (INCI name: steartrimonium bromide), lauryltrimethylammonium bromide (INCI name: lauryltrimonium bromide), isostearyllauryldimethylammonium chloride (INCI name: isostearyllauryldimonium chloride), dicetyldimethylammonium chloride (INCI name: dicetyldimonium chloride), distearyldimethylammonium chloride (INCI name: distearyldimonium chloride), and dicocoyl dimethylammonium chloride (INCI name: dicocodimonium chloride).

The component (F) is preferably monoalkyltrimethylammonium chloride and monoalkyltrimethylammonium bromide. Inter alia, stearyltrimethylammonium chloride (INCI name: steartrimonium chloride), cetyltrimethylammonium chloride (INCI name: cetrimonium chloride), and lauryltrimethylammonium chloride (INCI name: lauryltrimonium chloride) are more preferable.

The component (F) may be used alone or in combination of two or more, and may be included in any of the first agent, the second agent, and the third agent. From the viewpoint of spreadability toward hair tip of the mixture applied to the root of hair, the content of the component (F) in the mixture of the first agent and the second agent is preferably 0.05% by mass or more, more preferably 0.10% by mass or more, and even more preferably 0.2% by mass or more. It is preferably 5% by mass or less, more preferably 4% by mass or less, and even more preferably 3% by mass or less.

[Higher Fatty Acid and Salts Thereof]

From the viewpoint of spreadability toward hair tip of the mixture applied to the root of hair, the cosmetic product for hair dyeing or hair bleaching of the present invention may contain a higher fatty acid or salts thereof in the mixture of the first agent and the second agent. Examples of the salts of the higher fatty acid include basic salts of fatty acids having 8 to 22 carbon atoms. Specifically, examples of the salts include basic salts of a single fatty acid such as lauric acid, myristic acid, palmitic acid, isostearic acid, and oleic acid, and basic salts of mixed fatty acids such as cocoyl fatty acid, and beef tallow fatty acid. The salts include inorganic basic salts such as sodium and potassium, an ammonium salt, an ethanolamine salt, a diethanol amine salt, triethanolamine salt, alkanolamine salts such as 2-amino-2-methyl propanol, and 2-amino-2-methyl propanediol, and basic amino acids such as lysine and arginine.

The higher fatty acid or salts thereof may be used alone or in combination of two or more, and may be included in any of the first agent, the second agent, and the third agent. From the viewpoint of spreadability toward hair tip of the mixture applied to the root of hair, the content of the higher fatty acid or salts thereof in the mixture of the first agent and the second agent is preferably 0.1% by mass or more, more preferably 0.3% by mass or more, and even more preferably 0.5% by mass or more, and it is preferably 10% by mass or less, more preferably 8% by mass or less, and even more preferably 6% by mass or less.

[Nonionic Surfactant Other Than Component (D)]

The cosmetic product for hair dyeing or hair bleaching of the present invention may further contain a nonionic surfactant other than the component (D) in the mixture of the first agent and the second agent.

Examples of the nonionic surfactant other than the component (D) include a polyethoxylate and an alkyl glycoside of a secondary alcohol represented by the following general formula (8):

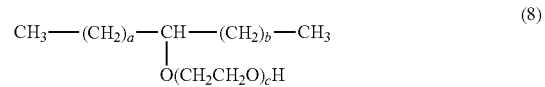

$$CH_3-(CH_2)_a-\underset{O(CH_2CH_2O)_cH}{CH}-(CH_2)_b-CH_3 \qquad (8)$$

wherein a and b are the number of 7 or more and 21 or less in total, and c represents a weight average number of between 6 or more and 16 or less.

The total number of a and b in the general formula (8) is preferably 7 or more, and more preferably 9 or more. It is preferably 19 or less, and more preferably 15 or less. Subscript c is preferably 8 or more, and it is preferably 12 or less, and more preferably 10 or less. The polyethoxylate of a secondary alcohol which can be preferably used includes polyoxyethylene tridecyl ether (Softanol 90 from NIPPON SHOKUBAI CO., LTD.; a+b=9 to 11, and c=9 in the general formula (8)).

The alkylglucoside which can be preferably used includes an alkylglycoside having an average alkyl carbon atom number of 8 or more and 16 or less, and sugar average condensation degree of 1 or more and 2 or less.

[Amphoteric Surfactant]

The cosmetic product for hair dyeing or hair bleaching of the present invention may further contain an amphoteric surfactant in the mixture of the first agent and the second agent.

Examples of the amphoteric surfactant include carbobetaine, amidobetaine, sulfobetaine, hydroxysulfobetaine, amidosulfobetaine, phosphobetaine, imidazolinium, and amine oxide surfactants having an alkyl group, an alkenyl group, or an acyl group having 8 or more and 24 or less carbon atoms. Inter alia, carbobetaine-based surfactants and sulfobetaine-based surfactants are preferable. Examples of the preferable amphoteric surfactants include laurylamidopropyl betaine, cocamidopropyl betaine, lauryldimethylaminoacetic acid betaine, and laurylhydroxysulfobetaine.

The amphoteric surfactant may be used alone or in combination of two or more, and may be included in any of the first agent, the second agent, and the third agent. From the viewpoint of application properties of the hair dye, the content of the amphoteric surfactant in the mixture of the first agent and the second agent is preferably 0.01% by mass or more, and more preferably 0.1% by mass or more. It is preferably 20% by mass or less, more preferably 15% by mass or less, and even more preferably 10% by mass or less.

[Dye]

When the cosmetic product for hair dyeing or hair bleaching of the present invention is a cosmetic product for hair dyeing, it contains an oxidative dye intermediate or a direct dye in the first agent.

(Oxidative Dye Intermediate)

As an oxidative dye intermediate, a known precursor and a known coupler, which are generally used in hair dyes, can be used. Examples of the precursor include p-phenylenediamine, toluene-2,5-diamine, o-chloro-p-phenylenediamine, N-phenyl-p-phenylenediamine, N,N-bis(hydroxyethyl)-p-phenylenediamine, 3-methyl-4-aminophenol, 2-hydroxyethyl-p-phenylenediamine, p-aminophenol, p-methylaminophenol, 4-amino-m-cresol, o-aminophenol, and salts thereof.

Examples of the coupler include resorcin, methylresorcin, 1-naphthol, 1,5-dihydroxynaphthalene, 5-amino-o-cresol, m-phenylenediamine, o-aminophenol, m-aminophenol, p-aminophenol, 2,4-diaminophenoxyethanol, 2,6-diamino pyridine, 2-methyl-5-hydroxyethyl aminophenol, 2-amino-3-hydroxypyridine, and salts thereof.

Each of the precursor and the coupler may be used alone or in combination of two or more. The content of each of the precursor and the coupler in the first agent is preferably 0.01% by mass or more, and more preferably 0.1% by mass or more. It is preferably 5% by mass or less, and more preferably 4% by mass or less.

(Direct Dye)

Examples of the direct dye include an acidic dye, a nitro dye, a disperse dye, and a basic dye. More specifically, examples of the acidic dye include Blue No. 1, Violet No. 401, Black No. 401, Orange No. 205, Red No. 227, Red No. 106, Yellow No. 203, and Acid Orange 3. Examples of the nitro dye include 2-nitro-p-phenylenediamine, 2-amino-6-chloro-4-nitrophenol, 3-nitro-p-hydroxyethyl amino phenol, 4-nitro-o-phenylenediamine, 4-amino-3-nitrophenol, 4-hydroxypropyl amino-3-nitrophenol, HC BLUE NO. 2, HC ORANGE NO. 1, HC RED NO. 1, HC YELLOW NO. 2, HC YELLOW NO. 4, HC YELLOW NO. 5, HC RED NO. 3, and N,N-bis(2-hydroxyethyl)-2-nitro-p-phenylenediamine. Examples of the disperse dye include Disperse Violet 1, Disperse Blue 1, and Disperse Black 9. Examples of the basic dye include Basic Blue 99, Basic Brown 16, Basic Brown 17, Basic Red 76, Basic Yellow 76, Basic Orange 31, and Basic Red 51.

The direct dye may be used alone or in combination of two or more, and the direct dye may also be used in combination with an oxidative dye intermediate. The content of the direct dye in the first agent is preferably 0.001% by mass or more, and more preferably 0.01% by mass or more. It is preferably 5% by mass or less, and more preferably 3% by mass or less.

[Other Optional Components]

In addition to the above-described components, other components generally used as raw materials for cosmetic products can be added to the cosmetic product for hair dyeing or hair bleaching of the present invention. Examples of such optional components include oil agents, silicones, nonvolatile hydrophilic solvents, animal and vegetable oils and fats, natural or synthetic polymers, ethers, protein derivatives, hydrolyze proteins, amino acids, antiseptics, chelating agents, stabilizers, antioxidants, plant extracts, herbal extracts, vitamins, flavoring agents, and ultraviolet absorbers.

[pH]

The pH (25° C.) of the first agent of the cosmetic product for hair dyeing or hair bleaching of the present invention is preferably 8.5 or more and more preferably 9.0 or more, and it is preferably 11.5 or less, more preferably 11.0 or less, and even more preferably 10.8 or less, in terms of hair dyeing effect and suppression of skin irritation. The pH (25° C.) of the second agent is preferably 2 or more and more preferably 2.5 or more, and it is preferably 6 or less, and more preferably 4 or less, from the viewpoint of suppression of hydrogen peroxide decomposition. Furthermore, the pH (25° C.) of the mixture of the first agent and the second agent is preferably 8 or more and more preferably 9 or more, and it is preferably 12 or less, more preferably 11.0 or less, and even more preferably 10.5 or less, in terms of hair dyeing effect and skin irritation. Examples of a pH adjuster include, in addition to the above-described alkali agent, inorganic acids such as hydrochloric acid and phosphoric acid; organic acids such as citric acid, glycolic acid, and lactic acid; and phosphates such as potassium dihydrogen phosphate and disodium hydrogen phosphate.

[Viscosity]

Viscosity at 25° C. of any one of the first agent and the second agent of the present invention is 100 mPa·s or less, and viscosity at 25° C. of the other agent is 1000 mPa·s or more.

(Viscosity of the Agent Having Viscosity at 25° C. of 100 mPa·s or Less)

The viscosity of the agent having viscosity at 25° C. of 100 mPa·s or less is defined by the value obtained by using BROOKFIELD VISCOMETER (Model: LV DV-I Prime, manufactured by BROOKFIELD) after rotation for 1 minute at 25° C. with LV SPINDLE (62) under the condition of at a rotation rate of 60 rpm.

The viscosity of the agent having viscosity at 25° C. of 100 mPa·s or less is preferably 1 mPa·s or more, more preferably 2 mPa·s or more, and even more preferably 3 mPa·s or more, and it is preferably 95 mPa·s or less, more preferably 90 mPa·s or less, and even more preferably 85 mPa·s or less, from the viewpoint of ease of mixing.

(Viscosity of the Agent Having Viscosity at 25° C. of 1000 mPa·s or More)

The viscosity of the agent having viscosity at 25° C. of 1000 mPa·s or more is defined by the value obtained by using BROOKFIELD VISCOMETER (Model: RV DV-I Prime, manufactured by BROOKFIELD) equipped with a helical stand after rotation for 1 minute at 25° C. with HELIPATH SPINDLE (T-bar spindle C (93)) under the condition of at a rotation rate of 10 rpm.

The viscosity of the agent having viscosity at 25° C. of 1000 mPa·s or more is preferably 3000 mPa·s or more, more preferably 5000 mPa·s or more, and even more preferably 10000 mPa·s or more, and it is preferably 35000 mPa·s or less, more preferably 30000 mPa·s or less, even more preferably 25000 mPa·s or less, and even more preferably 20000 mPa·s or less, from the viewpoint of preventing dripping of the mixture.

(Viscosity at 25° C. of Mixture of First Agent and Second Agent)

The viscosity of the mixture of the first agent and the second agent is defined by the value obtained by using BROOKFIELD VISCOMETER (Model: RV DV-I Prime, manufactured by BROOKFIELD) equipped with a helical stand after rotation for 1 minute at 25° C. with HELIPATH SPINDLE (T-bar spindle C (93)) under the condition of at a rotation rate of 10 rpm. In the measurement, the first agent (48 g) and the second agent (72 g) are poured into a main body of a container having an inner capacity of 150 mL, and a cap unit having a tapered nozzle is mounted on the main body of the container. The mixture is prepared by shaking the container up and down for 10 to 50 times with the nozzle tip covered by hand. Then, the mixture is allowed to stand for 30 seconds, and then subjected to the above-described measurement.

The viscosity at 25° C. of the mixture is preferably 5000 mPa·s or more, more preferably 7000 mPa·s or more, even more preferably 9000 mPa·s or more, and even more preferably 20000 mPa·s or more, and it is preferably 35000 mPa·s or less, more preferably 33000 mPa·s or less, even more preferably 31000 mPa·s or less, and even more preferably 29000 mPa·s or less, from the viewpoint of both prevention of dripping of the mixture and spreadability of the mixture over the hair.

By controlling the viscosity of the mixture of the first agent and the second agent within the above-described range, spreadability toward hair tip of the mixture applied to hair can be achieved and dripping down of the mixture applied to hair can be suppressed. The viscosity of the mixture can be controlled within the above-described range by adding a water-soluble solvent or suitably controlling contents or types of the surfactants, polyols, and higher alcohols.

[Applicator]

The cosmetic product for hair dyeing or hair bleaching of the present invention can be packed into an applicator equipped with a tapered discharge unit so that the mixture can be directly applied to the root of hair. Examples of the applicator which can be used include that shown in FIG. 1 of Japanese Unexamined Utility Model Publication No. H6-65254 A.

The mixing ratio between the first agent and the second agent in the cosmetic product for hair dyeing or hair bleaching of the present invention is preferably from 1:4 to 4:1, and more preferably from 1:3 to 1:1, at a mass ratio.

[Method of Hair Bleaching or Hair Dyeing]

Pretreatment Step

A method of hair dyeing or hair bleaching of the present invention utilizes the cosmetic product for hair dyeing or hair bleaching of the present invention and includes the following steps (a) and (b). The method may include a step of untangling hair in advance as a pretreatment step. Consequently, when the mixture is spread toward hair tip after the mixture is applied to the root of the hair and allowed to stand for a certain period, the hair does not easily become entangled, and thus a risk of scattering of the mixture can be avoided.

Step (a)

Step (a) is a step of mixing the first agent and the second agent (and additionally the third agent in a three-agent cosmetic product) in a main body of a container. By setting the viscosity at 25° C. of one of the first agent and the second agent to 100 mPa·s or less, the other agent having the viscosity at 25° C. of 1000 mPa·s or more can be easily mixed together in the main body of the container. By shaking the main body of the container up and down for preferably 2 times or more, more preferably 3 times or more, and even more preferably 4 times or more, the first agent and a second agent (and additionally the third agent in a three-agent cosmetic product) can be definitely mixed together, which prevents uneven dyeing or uneven bleaching.

Step (b)

Step (b) is a step of extruding the mixture of the first agent and the second agent (and additionally the third agent in a three-agent cosmetic product) from an applicator including the main body of the container equipped with a cap unit having a tapered nozzle to apply the mixture to the root of hair. By using, for example, an applicator shown in FIG. 1 of JP H6-65254 A, the mixture can be properly applied to the root of hair.

Step (c)

After step (b), the method preferably includes a step of allowing the mixture applied to the root of hair to stand for from 1 to 30 minutes as step (c). By this step, the root of a newly grown hair, which is resistant to dyeing, can be more definitely dyed or bleached.

Step (d)

After step (c), the method preferably further includes a step of spreading the mixture present around the root of hair over the whole hair as step (d). Examples of step (d) include a step of rubbing the mixture on hair with hand.

Step (e)

After step (d), the method preferably further includes a step of allowing the mixture to stand for from 5 to 20 minutes as step (e). Here, from the viewpoint of further preventing dripping down during the period, it is preferable to rub the mixture into the hair with hand.

After these steps (a) and (b), preferably after steps (a) to (c), more preferably after steps (a) to (d), and even more preferably after steps (a) to (e), the mixture can be washed away, and then hair can be shampooed, conditioned, and rinsed with water at one's disposal, and the hair can be dried.

With respect to the above-described embodiments, preferable aspects of the present invention are further disclosed below.

<1> A cosmetic product for hair dyeing or hair bleaching including:

a first agent comprising an alkali agent; and a second agent comprising hydrogen peroxide, wherein viscosity at 25° C. of one of the first agent and the second agent is 100 mPa·s or less, and viscosity at 25° C. of the other agent is 1000 mPa·s or more, the cosmetic product comprises the following components (A) to (D) in a mixture of the first agent and the second agent, and a mass ratio of a total amount of the component (B) and the component (C) to the component (A), [(B)(C)]/(A), in the mixture is 2 or more and 11 or less:

(A) a polymer comprising a diallyl quaternary ammonium salt as a constitutional unit and having a charge density of 2.5 meq/g or more and 9 meq/g or less, (B) a compound represented by the following general formula (3):

$$R^5\text{—O—}(CH_2CH_2O)_n\text{—}[CH_2CH(CH_3)O]_m\text{—}SO_3M^1 \quad (3)$$

wherein $R^5$ represents a hydrocarbon group having 8 or more and 25 or less carbon atoms, n represents an average addition molar number of 0 or more and 50 or less, represents an average addition molar number of 0 or more and 50 or less, and $M^1$ represents an alkali metal or $NH_4$, (C) an anionic surfactant having carboxy group(s), and (D) a polyoxyethylene-based nonionic surfactant having an oxyethylene group of an average addition molar number of 90 or more and 250 or less.

<2> The cosmetic product for hair dyeing or hair bleaching according to <1>, wherein a charge density of the component (A) is preferably 3.0 meq/g or more, more preferably 3.5 meq/g or more, and even more preferably 4.5 meq/g or more, and it is preferably 8.0 meq/g or less, more preferably 7.0 meq/g or less, even more preferably 6.5 meq/g or less, even more preferably 6.0 meq/g or less, and even more preferably 5.5 meq/g or less.

<3> The cosmetic product for hair dyeing or hair bleaching according to <1> or <2>, wherein the polymer of the component (A) is preferably a polymer having a backbone represented by the following general formula (1) or (2):

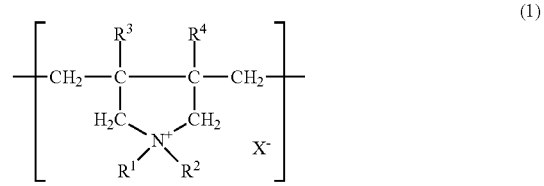

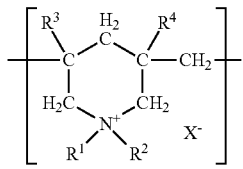
(2)

wherein $R^1$ and $R^2$ may be the same or different and represent a hydrogen atom, or an alkyl group, an aryl group (e.g., a phenyl group), a hydroxyalkyl group, an amidoalkyl group, a cyanoalkyl group, an alkoxyalkyl group, or a carboalkoxyalkyl group having 1 or more and 18 or less carbon atoms, $R^3$ and $R^4$ may be the same or different and represent a hydrogen atom, an alkyl group having 1 or more and 3 or less carbon atoms, or a phenyl group, and $X^-$ represents an anion (e.g., chloride ion, bromide ion, iodide ion, sulfate anion, sulfonate anion, methylsulfate anion, phosphoric acid anion, and nitrate anion).

<4> The cosmetic product for hair dyeing or hair bleaching according to <3>, wherein the polymer of the component (A) contains a constitutional unit represented by the formula (1) or (2) in an amount of preferably from 20 to 100 more preferably from 30 to 100 mol %, and even more preferably from 50 to 100 mol % in one molecule.

<5> The cosmetic product for hair dyeing or hair bleaching according to any one of <1> to <4>, wherein a weight-average molecular weight of the component (A) is preferably 40,000 or more, more preferably 200,000 or more, even more preferably 400,000 or more, even more preferably 2,000,000 or more, and even more preferably 4,000,000 or more, and it is preferably 50,000,000 or less, more preferably 10,000,000 or less, and even more preferably 5,000,000 or less.

<6> The cosmetic product for hair dyeing or hair bleaching according to <1> to <5>, wherein the content of the component (A) in the mixture of the first agent and the second agent is preferably 0.10% by mass or more, more preferably 0.125% by mass or more, and even more preferably 0.15% by mass or more, and it is preferably 5% by mass or less, more preferably 4% by mass or less, even more preferably 3% by mass or less, even more preferably 2% by mass or less, and even more preferably 1% by mass or less.

<7> The cosmetic product for hair dyeing or hair bleaching according to any one of <1> to <6>, wherein $R^5$ in the general formula (3) is preferably a linear or branched alkyl group or alkenyl group, and preferably a linear alkyl group, and the number of carbon atoms of $R^5$ is preferably 10 or more, and it is preferably 24 or less, more preferably 22 or less, and even more preferably 18 or less.

<8> The cosmetic product for hair dyeing or hair bleaching according to any one of <1> to <7>, wherein n in the general formula (3) is preferably 0.5 or more, and more preferably 1 or more, and it is preferably 45 or less, more preferably 30 or less, even more preferably 15 or less, even more preferably 10 or less, even more preferably 8 or less, and even more preferably 6 or less.

<9> The cosmetic product for hair dyeing or hair bleaching according to any one of <1> to <8>, wherein m in the general formula (3) is preferably 30 or less, more preferably 10 or less, even more preferably 5 or less, and even more preferably 0.

<10> The cosmetic product for hair dyeing or hair bleaching according to any one of <1> to <9>, wherein the content of the component (B) in the mixture of the first agent and the second agent is preferably 0.05% by mass or more, more preferably 0.1% by mass or more, even more preferably 0.2% by mass or more, even more preferably 0.3% by mass or more, even more preferably 0.5% by mass or more, even more preferably 0.8% by mass or more, and even more preferably 1.0% by mass or more, and it is preferably 10% by mass or less, more preferably 8% by mass or less, even more preferably 6% by mass or less, even more preferably 5% by mass or less, even more preferably 4% by mass or less, and even more preferably 3% by mass or less.

<11> The cosmetic product for hair dyeing or hair bleaching according to any one of <1> to <10>, wherein the component (C) is preferably at least one compound selected from the group consisting of an N-acylamino acid salt, an N-acyl-N-alkylamino acid salt, and an alkylether carboxylic acid salt.

<12> The cosmetic product for hair dyeing or hair bleaching according to any one of <1> to <11>, wherein the content of the component (C) in the mixture of the first agent and the second agent is preferably 0.05% by mass or more, more preferably 0.10% by mass or more, even more preferably 0.2% by mass or more, even more preferably 0.3% by mass or more, even more preferably 0.5% by mass or more, even more preferably 0.6% by mass or more, and even more preferably 1.0% by mass or more, and it is preferably 10% by mass or less, more preferably 8% by mass or less, even more preferably 6% by mass or less, even more preferably 5% by mass or less, even more preferably 4% by mass or less, and even more preferably 3% by mass or less.

<13> The cosmetic product for hair dyeing or hair bleaching according to any one of <1> to <12>, wherein the content of the total amount of the components (B) and (C) in the mixture of the first agent and the second agent is preferably 0.1% by mass or more, more preferably 0.2% by mass or more, even more preferably 0.4% by mass or more, even more preferably 0.6% by mass or more, even more preferably 0.8% by mass or more, even more preferably 1.0% by mass or more, and even more preferably 2.0% by mass or more, and it is preferably 15% by mass or less, more preferably 10% by mass or less, even more preferably 8% by mass or less, even more preferably 6% by mass or less, and even more preferably 4% by mass or less.

<14> The cosmetic product for hair dyeing or hair bleaching according to <1> to <13>, wherein the mass ratio of the component (B) to the total amount of the component (B) and the component (C), (B)/[(B)+(C)], in the mixture of the first agent and the second agent is preferably 0.1 or more, more preferably 0.2 or more, even more preferably 0.3 or more, and even more preferably 0.4 or more, and it is preferably 0.8 or less, more preferably 0.7 or less, and even more preferably 0.6 or less.

<15> The cosmetic product for hair dyeing or hair bleaching according to <1> to <14>, wherein the mass ratio of the total amount of the components (B) and (C) to the component (A), [(B)+(C)]/(A), in the mixture of the first agent and the second agent is preferably 2.2 or more, more preferably 2.4 or more, even more preferably 2.6 or more, even more preferably 2.8 or more, even more preferably 3.0 or more, and even more preferably 4 or more, and it is preferably 10 or less, and more preferably 9 or less.

<16> The cosmetic product for hair dyeing or hair bleaching according to any one of <1> to <15>, wherein the component (D) is preferably a polyoxyethylene-based nonionic surfactant represented by the following general formula (5):

$$R^7-O-(CH_2CH_2O)_r-H \qquad (5)$$

wherein R[7] represents a linear or branched saturated or unsaturated hydrocarbon group having 8 or more, preferably 10 or more, and more preferably 12 or more, and 22 or less, preferably 20 or less, and more preferably 18 or less carbon atoms, r represents an average number of 90 or more, preferably 95 or more, and more preferably 100 or more, and 250 or less, preferably 220 or less, more preferably 200 or less, and even more preferably 180 or less.

<17> The cosmetic product for hair dyeing or hair bleaching according to any one of <1> to <16>, wherein the content of the component (D) in the mixture of the first agent and the second agent is preferably 0.1% by mass or more, more preferably 0.2% by mass or more, even more preferably 0.3% by mass or more, and even more preferably 0.4% by mass or more, and it is preferably 10% by mass or less, more preferably 8% by mass or less, even more preferably 6% by mass or less, even more preferably 4% by mass or less, and even more preferably 3% by mass or less.

<18> The cosmetic product for hair dyeing or hair bleaching according to any one of <1> to <17>, preferably further including an aliphatic alcohol having 12 or more and 24 or less carbon atoms as a component (E) in the mixture of the first agent and the second agent.

<19> The cosmetic product for hair dyeing or hair bleaching according to <18>, wherein the component (E) is preferably represented by the following general formula (6):

$$R^8\text{—OH} \tag{6}$$

wherein R[8] is a linear or branched hydrocarbon group, preferably a linear or branched alkyl group or alkenyl group, and more preferably a linear alkyl group having 12 or more, and preferably 14 or more, and 24 or less, and preferably 22 or less carbon atoms.

<20> The cosmetic product for hair dyeing or hair bleaching according to <18> or <19>, wherein the content of the component (E) in the mixture of the first agent and the second agent is preferably 0.5% by mass or more, more preferably 1.0% by mass or more, and even more preferably 1.5% by mass or more, and it is preferably 20% by mass or less, more preferably 15% by mass or less, even more preferably 10% by mass or less, and even more preferably 8% by mass or less.

<21> The cosmetic product for hair dyeing or hair bleaching according to any one of <1> to <20>, preferably further including a quaternary ammonium salt type cationic surfactant as a component (F) in the mixture of the first agent and the second agent.

<22> The cosmetic product for hair dyeing or hair bleaching according to <21>, wherein the content of the component (F) in the mixture of the first agent and the second agent is preferably 0.05% by mass or more, more preferably 0.10% by mass or more, and even more preferably 0.2% by mass or more, and it is preferably 5% by mass or less, more preferably 4% by mass or less, and even more preferably 3% by mass or less.

<23> The cosmetic product for hair dyeing or hair bleaching according to any one of <1> to <22>, wherein the pH (25° C.) of the first agent is preferably 8.5 or more, and more preferably 9.0 or more, and it is preferably 11.5 or less, more preferably 11.0 or less, and even more preferably 10.8 or less; the pH (25° C.) of the second agent is preferably 2 or more, and more preferably 2.5 or more, and it is preferably 6 or less, and more preferably 4 or less; and the pH (25° C.) of the mixture of the first agent and the second agent is preferably 8 or more, and more preferably 9 or more, and it is preferably 12 or less, more preferably 11.0 or less, and even more preferably 10.5 or less.

<24> The cosmetic product for hair dyeing or hair bleaching according to any one of <1> to <23>, wherein the viscosity at 25° C. of any one agent of the first agent and the second agent is preferably 1 mPa·s or more, more preferably 2 mPa·s or more, and even more preferably 3 mPa·s or more, and it is preferably 95 mPa·s or less, more preferably 90 mPa·s or less, and even more preferably 85 mPa·s or less; and the viscosity at 25° C. of the other agent is preferably 3000 mPa·s or more, more preferably 5000 mPa·s or more, and even more preferably 10000 mPa·s or more, and it is preferably 35000 mPa·s or less, more preferably 30000 mPa·s or less, even more preferably 25000 mPa·s or less, and even more preferably 20000 mPa·s or less.

<25> The cosmetic product for hair dyeing or hair bleaching according to any one of <1> to <24>, wherein the viscosity at 25° C. of the mixture of the first agent and the second agent is preferably 5000 mPa·s or more, more preferably 7000 mPa·s or more, even more preferably 9000 mPa·s or more, and even more preferably 20000 mPa·s or more, and it is preferably 35000 mPa·s or less, more preferably 33000 mPa·s or less, even more preferably 31000 mPa·s or less, and even more preferably 29000 mPa·s or less.

<26> A method of using the cosmetic product for hair dyeing or hair bleaching according to any one of <1> to <25>, the method including applying the total amount of the mixture of the first agent and the second agent to the root of hair.

<27> A method of hair dyeing or hair bleaching including the following steps (a) and (b):

(a) a step of mixing the first agent and the second agent of the cosmetic product for hair dyeing or hair bleaching according to any one of <1> to <25> in a main body of a container, and (b) a step of extruding the above-described mixture from an applicator including the above-described main body of the container equipped with a cap unit having a tapered nozzle to apply the mixture to the root of hair.

<28> The method of hair dyeing or hair bleaching according to <27>, preferably further including a step of allowing the mixture applied to the root of hair to stand for from 1 to 30 minutes as step (c), after step (b).

<29> The method of hair dyeing or hair bleaching according to <27> or <28>, preferably further including a step of spreading the mixture present around the root of hair over the whole hair as step (d), after step (c).

<30> The method of hair dyeing or hair bleaching according to <29>, preferably further including a step of allowing the mixture to stand for 5 to 20 minutes as step (e) after step (d).

EXAMPLES

Examples 1 to 12, and Comparative Examples 1 to 6

First agents having formulations as shown in Table 1 and second agents having formulations as shown in Table 2 were prepared. Mixtures were prepared by mixing the first agents and the second agents in a mass ratio of 1:1.5.

Each mixture was prepared by charging a 30 mL beaker (diameter: 35 mm) manufactured by Kimble Chase with 10 g of the first agent and 15 g of the second agent and mixing 30 seconds with a plastic spatula (product number: 3005) manufactured by Corning Incorporated. The following evaluations were performed using these mixtures.

<Resistance to Dripping>

On the surface of a plastic film of COMPANE (registered trademark) manufactured by IPS Co., Ltd. (Arakawa-ku, Tokyo), 0.5 g of the mixture was applied within an area having a diameter of 2 cm or less. The COMPANE was held perpendicular to the ground and allowed to stand for 5 minutes, and then downward migration length of the mixture from the point of application was evaluated. The results of these evaluations are shown in Table 3.

4: The migration length is 5 cm or less.
3: The migration length is more than 5 cm and 10 cm or less.
2: The migration length is more than 10 cm and 15 cm or less.
1: The migration length is more than 15 cm.

A mixture with less migration length according to the above evaluation does not drip after applying to head, and can be held steadily on the head.

<Spreadability of Mixture>

To 10 g of tress (25 cm) manufactured by IHIP, 2 g of the mixture was applied to a portion within 3 cm from one end and allowed the mixture to stand for 5 minutes. Then, spreadability of the mixture was evaluated when the mixture was spread toward the other end with the tress being kneaded and loosened. The results of these evaluations are shown in Table 3.

4: A mixture can be spread over the area more than 20 cm from one end of tress.
3: A mixture can be spread over the area more than 15 cm and 20 cm or less from one end of tress.
2: A mixture can be spread over the area more than 10 cm and 15 cm or less from one end of tress.
1: A mixture can be spread over the area more than 5 cm and 10 cm or less from one end of tress.

A tress on which a mixture can be spread over a long distance according to the above evaluation can be dyed without color irregularity.

*1 to *7 shown in Table 1 are as follows.
*1: Lubrizol Advanced Materials, Inc., Merquat 280, charge density of 5.0 meq/g (active amount), MW: 4,500,000
*2: Lubrizol Advanced Materials, Inc., Merquat 295, charge density of 6.0 meq/g (active amount), MW: 190,000
*3: Lubrizol Advanced Materials, Inc., Merquat 100, charge density of 6.2 meq/g (active amount), MW: 150,000
*4: Lubrizol Advanced Materials, Inc., Merquat 740, charge density of 2.6 meq/g (active amount), MW: 120,000
*5: Lubrizol Advanced Materials, Inc., Merquat 550, charge density of 3.1 meq/g (active amount), MW: 1,600,000
*6: SEPPIC, Oramix NS 10
*7: Kao Corporation, EMULGEN 709

TABLE 1

| | Active amount (% by mass) | 1-1 | 1-2 | 1-3 | 1-4 | 1-5 | 1-6 | 1-7 | 1-8 | 1-9 | 1-10 | 1-11 | 1-12 | 1-13 | 1-14 | 1-15 |
|---|---|---|---|---|---|---|---|---|---|---|---|---|---|---|---|---|
| | Monoethanolamine | 5.51 | 5.51 | 5.51 | 5.51 | 5.51 | 5.51 | 5.51 | 5.51 | 5.51 | 5.51 | 5.51 | 5.51 | 5.51 | 2.40 | 2.40 |
| | Strong ammonia solution | 0.59 | 0.59 | 0.59 | 0.59 | 0.59 | 0.59 | 0.59 | 0.59 | 0.59 | 0.59 | 0.59 | 0.59 | 0.59 | 2.26 | 2.40 |
| | Ammonium chloride | 1.63 | 1.63 | 1.63 | 1.63 | 1.63 | 1.63 | 1.63 | 1.63 | 1.63 | 1.63 | 1.63 | 1.63 | 1.63 | 2.03 | 2.50 |
| (A) | Dimethyldiallyl-ammonium chloride/acrylic acid copolymer liquid (*1) | 1.20 | 1.20 | 1.20 | 0.20 | 1.20 | 1.20 | — | — | — | — | — | 1.20 | 1.20 | 1.20 | 1.20 |
| | Dimethyldiallyl-ammonium chloride/acrylic acid copolymer liquid (*2) | — | — | — | — | — | — | — | 1.2 | — | — | — | — | — | — | — |
| | Polychlorinated dimethylmethylene-piperidinium liquid (*3) | — | — | — | — | — | — | — | — | — | — | 1.2 | — | — | — | — |
| | Dimethyldiallyl-ammonium chloride/acrylamide copolymer liquid (*4) | — | — | — | — | — | — | — | — | — | 1.2 | — | — | — | — | — |
| | Dimethyldiallyl-ammonium chloride/acrylamide copolymer liquid (*5) | — | — | — | — | — | — | — | — | — | — | — | 1.2 | — | — | — |
| (B) | Sodium polyoxyethylene (2) lauryl ether sulfate | 3.60 | 1.00 | 1.20 | 1.20 | 5.00 | — | 3.60 | 3.60 | 3.60 | 3.60 | 3.60 | 3.20 | 3.60 | 3.60 | 3.60 |
| (C) | Sodium cocoyl glutamate | 3.60 | 1.00 | 1.20 | 1.20 | 5.00 | — | 3.60 | 3.60 | 3.60 | 3.60 | 3.60 | 1.90 | 3.60 | 3.60 | 3.60 |
| | Alkylglucoside (*6) | — | — | — | — | — | — | — | — | — | — | — | 2.60 | — | 1.00 | 1.00 |
| (D') | Polyethylene alkyl ether (*7) | — | — | — | — | — | — | — | — | — | — | — | 11.50 | — | 2.00 | 2.00 |
| (E) | Myristyl alcohol | — | — | — | — | — | — | — | — | — | — | — | 0.30 | — | — | — |
| | Toluene-2,5-Diamine Sulfate | — | — | — | — | — | — | — | — | — | — | — | — | 2.75 | 1.09 | 0.001 |
| | p-Aminophenol | — | — | — | — | — | — | — | — | — | — | — | — | — | — | — |
| | Resorcinol | — | — | — | — | — | — | — | — | — | — | — | — | 0.80 | 0.40 | 0.002 |
| | 2-Methylresorcinol | — | — | — | — | — | — | — | — | — | — | — | — | — | 0.08 | — |
| | m-Aminophenol | — | — | — | — | — | — | — | — | — | — | — | — | 0.46 | 0.06 | — |
| | 2-Amino-3-Hydroxypyridine | — | — | — | — | — | — | — | — | — | — | — | — | — | 0.02 | — |

TABLE 1-continued

| Active amount (% by mass) | First agent | | | | | | | | | | | | | | |
|---|---|---|---|---|---|---|---|---|---|---|---|---|---|---|---|
| | 1-1 | 1-2 | 1-3 | 1-4 | 1-5 | 1-6 | 1-7 | 1-8 | 1-9 | 1-10 | 1-11 | 1-12 | 1-13 | 1-14 | 1-15 |
| 2-Amino-4-Hydroxyethyl-aminoanisole Sulfate | — | — | — | — | — | — | — | — | — | — | — | — | 0.29 | — | — |
| Propylene glycol | 2.50 | 2.50 | 2.50 | 2.50 | 2.50 | 2.50 | 2.50 | 2.50 | 2.50 | 2.50 | 2.50 | 2.50 | 2.50 | 2.50 | 2.50 |
| Polypropylene glycol | 2.50 | 2.50 | 2.50 | 2.50 | 2.50 | 2.50 | 2.50 | 2.50 | 2.50 | 2.50 | 2.50 | 2.50 | 2.50 | 2.50 | 2.50 |
| Ethanol | 5.00 | 5.00 | 5.00 | 5.00 | 5.00 | 5.00 | 5.00 | 5.00 | 5.00 | 5.00 | 5.00 | 5.00 | 5.00 | 5.00 | 5.00 |
| Ascorbic acid | 0.40 | 0.40 | 0.40 | 0.40 | 0.40 | 0.40 | 0.40 | 0.40 | 0.40 | 0.40 | 0.40 | 0.40 | 0.40 | 0.40 | 0.40 |
| Anhydrous sodium sulfite | 0.50 | 0.50 | 0.50 | 0.50 | 0.50 | 0.50 | 0.50 | 0.50 | 0.50 | 0.50 | 0.50 | 0.50 | 0.50 | 0.50 | 0.50 |
| Tetrasodium edetate dihydrate | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 |
| Flavoring agent | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| Purified water | q.s. | q.s. | q.s. | q.s. | q.s. | q.s. | q.s. | q.s. | q.s. | q.s. | q.s. | q.s. | q.s. | q.s. | q.s. |
| Viscosity (mPa · s) | 14.0 | 9.0 | 9.5 | 7.0 | 15.0 | 8.0 | 14.0 | 9.0 | 15.0 | 9.5 | 27.5 | 21.5 | 15.0 | 11.5 | 12.5 |

TABLE 2

| | Active amount (% by mass) | Second agent | | | | | | | |
|---|---|---|---|---|---|---|---|---|---|
| | | 2-1 | 2-2 | 2-3 | 2-4 | 2-5 | 2-6 | 2-7 | 2-8 |
| | Hydrogen peroxide | 5.70 | 5.70 | 7.35 | 9.00 | 5.70 | 5.70 | 5.70 | 5.70 |
| | Hydroxyethanediphosphonic acid | 0.04 | 0.04 | 0.04 | 0.04 | 0.04 | 0.04 | 0.04 | 0.04 |
| (D) | Polyoxyethylene (100) stearyl ether | 0.89 | 0.89 | 0.89 | 0.89 | 0.89 | — | — | — |
| | Polyoxyethylene (150) cetyl ether | — | — | — | — | — | 0.89 | — | — |
| (D') | Polyoxyethylene (80) cetostearyl ether | — | — | — | — | — | — | 0.89 | — |
| | Polyoxyethylene (40) cetyl ether | — | — | — | — | — | — | — | 0.89 |
| (E) | Cetyl alcohol | 2.50 | 2.63 | 3.00 | 3.00 | 4.00 | 2.50 | 2.50 | 2.50 |
| | Stearyl alcohol | 2.50 | 1.13 | 3.00 | 3.00 | 4.00 | 2.50 | 2.50 | 2.50 |
| | Behenyl alcohol | — | 1.25 | — | — | — | — | — | — |
| (F) | Cetyltrimethylammonium chloride | 0.60 | 0.60 | 0.60 | 0.60 | 0.60 | 0.60 | 0.60 | 0.60 |
| | Polyoxyethylene (2) cetyl ether | 0.65 | 0.65 | 0.65 | 0.65 | 0.65 | 0.65 | 0.65 | 0.65 |
| | Propylene glycol | 2.50 | 2.50 | 2.50 | 2.50 | 2.50 | 2.50 | 2.50 | 2.50 |
| | Salicylic acid | 0.015 | 0.015 | 0.015 | 0.015 | 0.015 | 0.015 | 0.015 | 0.015 |
| | Acetaminophen | 0.015 | 0.015 | 0.015 | 0.015 | 0.015 | 0.015 | 0.015 | 0.015 |
| | Sodium hydroxide or phosphoric acid | * | * | * | * | * | * | * | * |
| | Purified water | q.s. | q.s. | q.s. | q.s. | q.s. | q.s. | q.s. | q.s. |
| | Viscosity (mPa · s) | 16500 | 13600 | 18300 | 14500 | 20500 | 16900 | 17500 | 16900 |

*: an amount to make pH of the second agent of 3.3

TABLE 3

| | Examples | | | | | | | | | |
|---|---|---|---|---|---|---|---|---|---|---|
| | 1 | 2 | 3 | 4 | 5 | 6 | 7 | 8 | 9 | 10 |
| First agent | 1-1 | 1-3 | 1-5 | 1-8 | 1-9 | 1-10 | 1-11 | 1-3 | 1-12 | 1-13 |
| Second agent | 2-1 | 2-1 | 2-1 | 2-1 | 2-1 | 2-1 | 2-1 | 2-6 | 2-2 | 2-5 |
| (A) in mixture [% by mass] | 0.48 | 0.48 | 0.48 | 0.48 | 0.48 | 0.48 | 0.48 | 0.48 | 0.48 | 0.48 |
| (B) in mixture [% by mass] | 1.44 | 0.48 | 2.00 | 1.44 | 1.44 | 1.44 | 1.44 | 0.48 | 1.28 | 1.44 |
| (C) in mixture [% by mass] | 1.44 | 0.48 | 2.00 | 1.44 | 1.44 | 1.44 | 1.44 | 0.48 | 0.76 | 1.44 |
| (D) in mixture [% by mass] | 0.53 | 0.53 | 0.53 | 0.53 | 0.53 | 0.53 | 0.53 | 0.53 | 0.53 | 0.53 |
| (B) + (C) in mixture [% by mass] | 2.88 | 0.96 | 4.00 | 2.88 | 2.88 | 2.88 | 2.88 | 0.96 | 2.04 | 2.88 |
| [(B) + (C)]/(A) in mixture | 6.00 | 2.00 | 8.30 | 6.00 | 6.00 | 6.00 | 6.00 | 2.00 | 4.25 | 6.00 |
| (B)/[(B) + (C)] in mixture | 0.50 | 0.50 | 0.50 | 0.50 | 0.50 | 0.50 | 0.50 | 0.50 | 0.63 | 0.50 |
| Mixture viscosity (mPa · s) | 28508 | 5100 | 26600 | 14800 | 7600 | 7300 | 9500 | 6600 | 12500 | 20700 |
| Resistance to dripping | 4 | 3 | 4 | 3 | 3 | 3 | 3 | 3 | 3 | 4 |

TABLE 3-continued

| Spreadability of mixture | 4 | 3 | 4 | 4 | 4 | 4 | 4 | 3 | 4 | 4 |
|---|---|---|---|---|---|---|---|---|---|---|

| | Examples | | Comparative Examples | | | | | |
|---|---|---|---|---|---|---|---|---|
| | 11 | 12 | 1 | 2 | 3 | 4 | 5 | 6 |
| First agent | 1-14 | 1-15 | 1-2 | 1-4 | 1-6 | 1-7 | 1-3 | 1-3 |
| Second agent | 2-3 | 2-4 | 2-1 | 2-1 | 2-1 | 2-1 | 2-7 | 2-8 |
| (A) in mixture [% by mass] | 0.48 | 0.48 | 0.48 | 0.08 | 0.48 | 0 | 0.48 | 0.48 |
| (B) in mixture [% by mass] | 1.44 | 1.44 | 0.40 | 0.48 | 0 | 1.44 | 0.48 | 0.48 |
| (C) in mixture [% by mass] | 1.44 | 1.44 | 0.40 | 0.48 | 0 | 1.44 | 0.48 | 0.48 |
| (D) in mixture [% by mass] | 0.53 | 0.53 | 0.53 | 0.53 | 0.53 | 0.53 | 0 | 0 |
| (B) + (C) in mixture [% by mass] | 2.88 | 2.88 | 0.80 | 0.96 | 0 | 2.88 | 0.96 | 0.96 |
| [(B) + (C)]/(A) in mixture | 6.00 | 6.00 | 1.67 | 12.00 | 0 | — | 2.00 | 2.00 |
| (B)/[(B) + (C)] in mixture | 0.50 | 0.50 | 0.50 | 0.50 | — | 0.50 | 0.50 | 0.50 |
| Mixture viscosity (mPa·s) | 16500 | 14200 | 4500 | 2500 | 1600 | 1900 | 3500 | 3800 |
| Resistance to dripping | 3 | 3 | 2 | 1 | 1 | 1 | 2 | 2 |
| Spreadability of mixture | 4 | 4 | 3 | 1 | 1 | 3 | 2 | 2 |

The invention claimed is:

1. A cosmetic product for hair dyeing or hair bleaching comprising:
a first agent comprising an alkali agent; and a second agent comprising hydrogen peroxide,
wherein a viscosity at 25° C. of one of the first agent and the second agent is 100 mPa·s or less, a viscosity at 25° C. of the other agent is 1000 mPa·s or more, and a viscosity at 25° C. of a mixture of the first agent and the second agent is 5000 mPa·s to 35000 mPa·s,
wherein a mixture of said first agent and said second agent comprises components (A) to (D), and a mass ratio of a total amount of the component (B) and the component (C) to the component (A), [(B)+(C)]:(A), in said mixture is 2:1 to 11:1,
(A) a polymer comprising a diallyl quaternary ammonium salt as a constitutional unit and having a charge density of 2.5 meq/g to 9 meq/g,
(B) a compound represented by formula (3):

wherein $R^5$ represents a hydrocarbon group having 8 to 25 carbon atoms, n represents an average addition molar number of 0 to 50, m represents an average addition molar number of 0 to 50, and $M^1$ represents an alkali metal or $NH_4$,
(C) an anionic surfactant having carboxy group(s), and
(D) a polyoxyethylene-based nonionic surfactant wherein the average addition molar number of the oxyethylene group is 90 to 250.

2. The cosmetic product for hair dyeing or hair bleaching according to claim 1, wherein a mass ratio of said component (B) to the total amount of said component (B) and said component (C), (B):[(B)+(C)], in said mixture of said first agent and said second agent is 0.1:1 to 0.8:1.

3. The cosmetic product for hair dyeing or hair bleaching according to claim 1, further comprising an aliphatic alcohol having 12 to 24 carbon atoms as a component (E) in the mixture of the first agent and the second agent.

4. The cosmetic product for hair dyeing or hair bleaching according to claim 3, wherein a content of said component (E) in said mixture of said first agent and said second agent is 0.5% by mass to 20% by mass, based on the total mass of said mixture.

5. The cosmetic product for hair dyeing or hair bleaching according to claim 1, further comprising a quaternary ammonium salt type cationic surfactant as a component (F) in the mixture of the first agent and the second agent.

6. The cosmetic product for hair dyeing or hair bleaching according to claim 5, wherein a content of said component (F) in said mixture of said first agent and said second agent is 0.05% by mass to 5% by mass, based on the total mass of said mixture.

7. The cosmetic product for hair dyeing or hair bleaching according to claim 1, wherein a charge density of the component (A) is 8.0 meq/g or less.

8. The cosmetic product for hair dyeing or hair bleaching according to claim 1, wherein said polymer of the component (A) is a polymer having a backbone represented by formula (1) or (2):

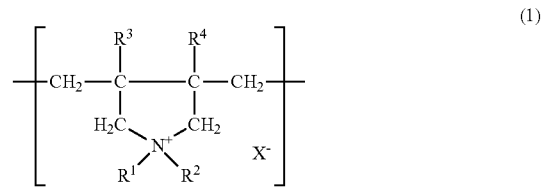

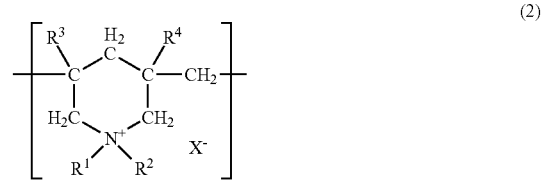

wherein $R^1$ and $R^2$ may be the same or different and represent a hydrogen atom, or an alkyl group, an aryl group, a hydroxyalkyl group, an amidoalkyl group, a cyanoalkyl group, an alkoxyalkyl group, or a carboalkoxyalkyl group having 1 to 18 carbon atoms, $R^3$ and $R^4$ may be the same or different and represent a hydrogen atom, an alkyl group having 1 to 3 carbon atoms, or a phenyl group, and $X^-$ represents an anion selected from the group consisting of chloride, iodide, sulfate, sulfonate, methylsulfate, phosphate, and nitrate.

9. The cosmetic product for hair dyeing or hair bleaching according to claim 8, wherein the polymer of the component (A) comprises a constitutional unit represented by the formula (1) or (2) in an amount of 20 mol % to 100 mol % in one molecule.

10. The cosmetic product for hair dyeing or hair bleaching according to claim 1, wherein a content of said component (A) in said mixture of said first agent and said second agent is 0.1% by mass to 5% by mass, based on the total mass of said mixture.

11. The cosmetic product for hair dyeing or hair bleaching according to claim 1, wherein a content of said component (B) in said mixture of said first agent and said second agent is 0.05% by mass to 10% by mass, based on the total mass of said mixture.

12. The cosmetic product for hair dyeing or hair bleaching according to claim 1, wherein the component (C) is at least one compound selected from the group consisting of an N-acylamino acid salt, an N-acyl-N-alkylamino acid salt, and an alkylether carboxylic acid salt.

13. The cosmetic product for hair dyeing or hair bleaching according to claim 1, wherein a content of said component (C) in said mixture of said first agent and said second agent is 0.05% by mass to 10% by mass, based on the total mass of said mixture.

14. The cosmetic product for hair dyeing or hair bleaching according to claim 1, wherein the total content of said component (B) and said component (C) in said mixture of said first agent and said second agent is 2.0% by mass to 15% by mass, based on the total mass of said mixture.

15. The cosmetic product for hair dyeing or hair bleaching according to claim 1, wherein a content of said component (D) in said mixture of said first agent and said second agent is 0.1% by mass to 10% by mass, based on the total mass of said mixture.

16. The cosmetic product for hair dyeing or hair bleaching according to claim 1, wherein the viscosity at 25° C. of one of the first agent and the second agent is 1 mPa·s to 95 mPa·s, and the viscosity at 25° C. of the other agent is 3000 mPa·s to 35000 mPa·s.

17. The cosmetic product for hair dyeing or hair bleaching according to claim 1, wherein the mass ratio of the total amount of said component (B) and said component (C) to said component (A), [(B)+(C)]:(A), in said mixture of said first agent and said second agent is 4:1 to 11:1.

18. A method of hair dyeing or hair bleaching, comprising applying a mixture of the first agent and the second agent according to claim 1 to a root of hair.

19. A method of hair dyeing or hair bleaching comprising (a) and (b):
   (a) mixing the first agent and the second agent of the cosmetic product for hair dyeing or hair bleaching according to claim 1 in a main body of a container, and
   (b) extruding the mixture from an applicator comprising the main body of the container equipped with a cap unit having a tapered nozzle to apply the mixture to a root of hair.

20. The method of hair dyeing or hair bleaching according to claim 19, further comprising (c) after (b):
   (c) allowing the mixture applied to the root of hair to stand for 1 to 30 minutes.

21. The method of hair dyeing or hair bleaching according to claim 20, further comprising (d) after (c):
   (d) spreading the mixture present around the root of hair over a whole hair.

\* \* \* \* \*